United States Patent [19]

Pluim, Jr.

[11] Patent Number: 4,472,507
[45] Date of Patent: Sep. 18, 1984

[54] METHOD FOR DETECTING EXPOSURE TO POISON IVY AND THE LIKE

[76] Inventor: Arthur W. Pluim, Jr., 602 W. Hickory, Stillwater, Minn. 55082

[21] Appl. No.: 270,218

[22] Filed: Jun. 4, 1981

[51] Int. Cl.³ .................... G01N 33/52; A61B 5/00
[52] U.S. Cl. .................... 436/131; 128/743; 424/9; 436/169; 436/183; 436/904
[58] Field of Search ............ 23/230 B, 230 M, 230 R, 23/932; 422/56, 57; 436/131, 183, 169; 424/9; 128/743; 436/904

[56] References Cited

U.S. PATENT DOCUMENTS

| | | | |
|---|---|---|---|
| 3,329,486 | 7/1967 | Rupe | 422/56 |
| 3,420,635 | 1/1969 | Davis | 422/56 |
| 3,847,552 | 11/1974 | Hobgood et al. | 422/56 X |
| 3,894,531 | 7/1975 | Saunders, Jr. | 128/743 |
| 3,912,457 | 10/1975 | Ogawa et al. | 422/56 |
| 3,914,174 | 10/1975 | Fuchs | 210/658 |
| 3,954,412 | 5/1976 | Ogawa et al. | 23/230 B X |
| 4,055,394 | 10/1977 | Friedman et al. | 422/56 |
| 4,092,119 | 5/1978 | Baier et al. | 422/56 |
| 4,259,318 | 3/1981 | Duhe et al. | 424/94 |
| 4,319,883 | 3/1982 | Imai et al. | 23/230 B |

OTHER PUBLICATIONS

Weiss et al., Chemical Abstracts, vol. 35, No. 9, 1941, No. 4840'.
Corbett et al., Journal of Pharmaceutical Sciences, vol. 64, No. 10, Oct. 1975, pp. 1715–1718.

Primary Examiner—Arnold Turk

[57] ABSTRACT

An indicator (10) for detecting contact with a naturally occurring polyhydroxyaromatic skin irritant or toxin like that found in poison ivy and the like comprises a carrier (12) treated with a reactant, such as ferric nitrate which reacts with the toxin and produces a distinct color change indicative of such contact.

6 Claims, 1 Drawing Figure

METHOD FOR DETECTING EXPOSURE TO POISON IVY AND THE LIKE

TECHNICAL FIELD

The present invention relates to a technique for detecting exposure to toxins, and particularly to a method and product for detecting contact with toxins of the type naturally present in the sap of poison ivy, poison oak, poison sumac and the like, whereby a chemically treated indicator is worn which changes color to signal such contact so that preventative measures can be undertaken promptly to minimize any allergic reaction stemming from contact with plants of this type.

BACKGROUND ART

A hazard traditionally associated with outdoor activities such as hiking and camping has been the possibility of exposure to poison ivy, poison oak, poison sumac and the like, which plants are in the rhus toxicodendron family. The sap of such plants contains a toxin which can cause an allergic reaction upon contact with the skin, despite the fact that the toxic substance naturally occurs in low concentrations (e.g., 2-5% of the sap) and the contact is usually brief and incidental. The extent of reaction varies from individual to individual. Some individuals may experience little or no reaction or simply some itching which disappears after a few days, while other develop a severe skin rash which may require treatment with antibiotics and may need several weeks or even months fully to heal. Unfortunately, one typically does not realize he has been exposed to poison ivy and the like until the symptoms develop some time after contact.

The most common approach to this problem has been to avoid any contact with such plants, which approach is extremely practical but not always workable under the circumstances. The leaves of poison ivy, for example, are similar to the foliage of other harmless plants and thus may not be readily distinguishable. Various medications are available for treating the effects of contact with these plants. In addition, techniques like that disclosed in U.S. Pat. No. 2,451,955 have been developed for determining in advance the sensitivity of individuals to poison ivy and the like.

Although the benefits of early treatment have been widely appreciated, little effort has been expended heretofore in developing a technique by which an individual would be promptly alerted to his having just contacted poison ivy, poison oak, poison sumac or the like. Early realization of such contact would enable an individual to wash the affected area and/or apply suitable medication, thereby limiting spread of any rash, shortening its duration and otherwise minimizing the allergic reaction.

SUMMARY OF THE INVENTION

The present invention comprises a technique for the early detection and visual indication of contact with a naturally occurring toxin which overcomes the foregoing and other difficulties associated with the prior art.

In accordance with the invention, there is provided an indicator which can be worn for detecting and signaling, through a visually observable color change, contact with poison ivy, poison oak, poison sumac and the like. The indicator comprises a carrier that provides a chemical reactant which promptly reacts and darkens upon contact in a natural environment with a naturally occurring concentration of the toxin found in the sap of such plants.

The carrier can be any suitable carrier, such as a liquid, gel, paste, aerosol or substrate, such as a strip of paper, cloth or foamed plastic. When a substrate is used, it will preferably include a layer of adhesive with a peel-away backing to facilitate attachment to the user in a position which is likely to contact the poisonous plants, if present.

The reactant will be any chemical that reacts on contact with catechol or a substituted catechol to give a visually observable color change. The reactant will often comprise a metallic salt, such as ferric nitrate, which can be applied to the carrier substrate in any manner.

One convenient manner of applying the reactant to a substrate is by dissolving the reactant in a solvent and then coating or soaking the carrier with the solution to deposit an effective amount of reactant which will react as desired.

BRIEF DESCRIPTION OF DRAWING

A better understanding of the invention can be had by reference to the following Detailed Description in conjunction with the accompanying Drawing, wherein the figure represents a perspective view of the poison ivy indicator of the invention.

DETAILED DESCRIPTION

Figure 1:
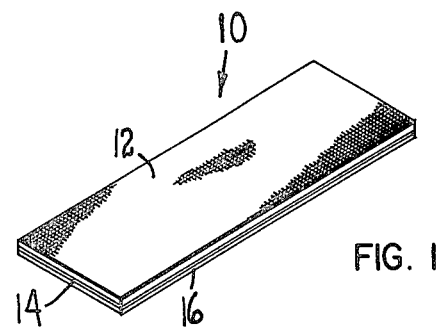

As previously mentioned, the present invention involves an indicator incorporating a chemical reactant, which will react in the presence of catechol or substituted catechols to produce a visually observable color change.

Although the indicator may be associated with any suitable carrier, such as a liquid (e.g., a sun screen or insect repellent), a gel, a salve, an aerosol or a substrate (e.g., paper), the use of indicators that include a substrate is preferred. Consequently, the present invention is described with particular reference to such indicators.

As previously indicated, the indicator will often comprise a substrate treated with an effective amount of reactant which, upon contact in a natural environment with a naturally occurring concentration of plant toxin (usually a catechol derivative), reacts and changes color to provide a positive visual indicator, thereby alerting the wearer of such contact. The sap of poison ivy and the like contains a polyhydroxyaromatic skin irritant or toxin.

Consequently, any chemical which readily reacts in the presence of the toxin to form a colored species would be suitable for the reactant, and several specific examples are set forth below.

Referring now to the Drawing, there is shown an indicator 10 representing a first embodiment of the invention. Indicator 10 is of fairly simple, inexpensive construction and is adapted for promptly detecting and signaling contact with the toxic sap of poison ivy, poison oak, poison sumac and other plants in the rhus toxicodendron family. The indicator 10 comprises a treated carrier substrate 12 which is worn or otherwise used to detect contact with the foregoing poisonous plants. The carrier substrate 12 can be formed of any material which can be coated, impregnated or otherwise treated with the reactant to be described in further detail hereinbelow. Porous materials such as paper, cloth or foamed plastics (e.g., flexible polyurethane) are suitable for use as the carrier substrate 12. Filter paper such as type 909-20 paper from Eaton-Dikeman Company of Mount Holly Springs, Pennsylvania has been found satisfactory.

The particular dimensions of the carrier substrate 12 are not critical to the practice of the invention, however, all sizes are not equally practical. A carrier substrate 12 which is too large can interfere with the movement of the wearer, while one which is too small may not be readily visible. As an example, a suitable size for substrate 12 is about one inch wide by three inches long by 0.002 inch thick.

The indicator 10 preferably includes a layer of adhesive 14 on one side of carrier substrate 12 together with a peel-away liner or backing 16 over the adhesive for convenience in applying the indicator to a suitable location, such as the shoes or shirt or skin. Any suitable commerically available adhesive having a liner on one side thereof can be utilized. For example, suitable transfer adhesive or double sided tape on a liner can be obtained from 3M Company in St. Paul, Minn. Once the backing 16 is peeled away, indicator 10 can readily be applied to virtually any place on the wearer which is likely to be affected if poison ivy, poison oak, or poison sumac is encountered.

While indicator 10 has been illustrated with adhesive 14 and backing 16, it will be understood that substrate 12 can be pinned to a wearer or worn in any other suitable manner.

An important feature of the present invention comprises the reactant which is utilized to treat the carrier substrate 12 of indicator 10. Any chemical which reacts upon contact with the natural skin irritant or toxin in poison ivy, poison oak, poison sumac and the like to produce a visual color change can be used. The chemical structure of such toxin contains an aromatic ring, and reactants which interact with the hydroxyl groups therein and undergo a distinct color change have been found satisfactory. Not all possible reactants work equally well when considerations of stability, sensitivity, reaction time, cost and nontoxicity to the wearer are taken into account. To be effective, however, a suitable reactant must produce a distinct color change promptly (within less than thirty minutes, usually in less than ten minutes) after contact. Thus, a very desirable reactant is one which provides a positive visual indication by a distinct color change within less than five minutes after contact with toxic sap (e.g., less than one minute after contact). It has been found through experimentation that metallic salts react nearly immediately with toxin in the sap of such plants, producing a distinct color change which can readily be observed and understood by an individual as meaning that contact with a poisonous plant has occurred. The metallic salts which will be discussed below have all been found to be stable, sensitive to the low natural concentrations of such toxin, and reliable in the sense of being relatively free from false positive indications.

Solutions of ferric salts work well. Such reactants are conveniently applied to the carrier substrate 12 by means of solution containing an effective concentration of the selected reactant. For example, the carrier substrate 12 can be soaked with a solution prepared of approximately 20% by weight ferric ammonium citrate, ferric chloride or ferric nitrate in water. Aqueous solutions ranging between about 6% and 36% (e.g., 10-30%) by weight of such compounds have been found effective, with concentrations below this range exhibiting insufficient sensitivity and concentrations beyond this range being wasteful of the reactant. Of these three compounds, ferric nitrate is preferred because of its excellent color change reaction, longer term stability, moderate toxicity and availability.

After a suitable reactant has been prepared, it is applied to the carrier substrate 12 and allowed to dry. The carrier substrate 12 is typically soaked with the liquid reactant so that the chemical reactant permeates the fibers thereof, however, the substrate can be coated or otherwise treated in any manner which deposits a sufficient amount of reactant to achieve the desired reaction. After treatment, the carrier substrate 12 is allowed to dry. The ferric salt compounds mentioned above typically dry to a light yellow color. (Upon contact with a poisonous plant, a reaction takes place relatively quickly which is accompanied by a color change as the thus treated carrier substrate 12 darkens.)

Although not wishing to be bound to any particular theory, it is believed that the toxin, which contains a reducing agent, causes the reduction and permits the subsequent rapid oxidation of the metallic compound. In other cases, it is believed that the hydroxyl (OH) groups on the aromatic ring of the naturally occurring toxin in the sap may complex with the metallic cation to form the color species which indicates contact with the skin irritant. However, color changes may occur in other ways.

Another suitable reactant is cupric chloride, which is also easily applied via an aqueous solution of similar concentration. The indicator 10 treated with cupric chloride reacts in similar fashion to the ferric compounds described in the preceding paragraph.

Another suitable reactant is ferric acetate, which can be dissolved in alcohol to facilitate application to substrate 12; however, an indicator 10 treated with this reactant exhibits sensitivity to light and thus is not as practical as the other ferric and cupric compounds mentioned above.

In addition to the above, diazammonium salts and oxidizing agents capable of interacting with polyhydroxyaromatic skin irritants to produce a color change can be used.

In other embodiments, the color forming reactant can be included in other carriers and applied to the skin or to clothing. For example, the reactant may be sprayed on, applied as an oil or cream, etc.

From the foregoing, it will thus be apparent that the present invention comprises a technique for the rapid detection of contact with toxic plants such as poison ivy and the like. The indicator herein is inexpensive in construction and utilizes a chemical reactant which provides a positive, reliable indication of toxic contact so that preventative measures can be undertaken immediately to minimize the allergic reaction which usually occurs following contact with such plants.

Although particular embodiments of the invention have been illustrated and described herein, it will be understood that the invention is not limited to the embodiments disclosed, but is intended to encompass any rearrangements, modifications, or substitutions of elements falling within the scope of the invention as defined by the following claims.

I claim:

1. A method for detecting the presence of naturally occurring polyhydroxyaromatic toxin in a natural environment comprising the steps of:

(a) applying to a surface an indicator comprising a carrier including a reactant of a type and in an amount sufficient to produce a visually observable color change in less than thirty minutes after being contacted with said toxin, (b) exposing said surface to said environment, and (c) observing for said color change.

2. A method in accordance with claim 1, wherein said toxin is found in poison ivy, poison oak, or poison sumac.

3. A method in accordance with claim 1, wherein said reactant is selected from ferric nitrate, ferric chloride, ferric ammonium citrate, ferric acetate, or cupric chloride.

4. A method in accordance with claim 1, wherein said carrier comprises a substrate selected from paper, cloth, or foamed plastic.

5. A method in accordance with claim 4, wherein said substrate carries an adhesive layer covered by a peel-away backing.

6. A method for detecting the presence of a naturally occurring polyhydroxyaromatic toxin comprising the steps of:

(a) exposing to an environment containing said toxin an indicator comprising a carrier including a reactant of a type and in an amount sufficient to produce a visually observable color change in less than thirty minutes after being contacted with a polyhydroxyaromatic toxin, and (b) observing for a color change in said indicator.

* * * * *